(12) United States Patent
McGarry et al.

(10) Patent No.: US 6,569,674 B1
(45) Date of Patent: May 27, 2003

(54) METHOD AND APPARATUS FOR PERFORMING BIOLOGICAL REACTIONS ON A SUBSTRATE SURFACE

(75) Inventors: Mark W. McGarry, Scottsdale, AZ (US); W. Travis Johnson, Chandler, AZ (US); George W. Hawkins, Gilbert, AZ (US)

(73) Assignee: Amersham Biosciences AB, Uppsala (SE)

( * ) Notice: Subject to any disclaimer, the term of this patent is extended or adjusted under 35 U.S.C. 154(b) by 0 days.

(21) Appl. No.: 09/492,013

(22) Filed: Jan. 26, 2000

Related U.S. Application Data (63) Continuation-in-part of application No. 09/464,490, filed on Dec. 15, 1999.

(51) Int. Cl.$^7$ .............................. C12Q 1/68; C12M 1/34; C12P 19/34; C07H 21/02; C07H 21/04
(52) U.S. Cl. ..................... 435/287.2; 435/6; 435/7.1; 435/91.1; 435/91.2; 435/285.1; 536/22.1; 536/23.1; 536/24.3; 536/24.31; 536/24.32; 536/24.33
(58) Field of Search ............................ 435/6, 7.1, 91.1, 435/91.2, 285.1, 287.2; 536/22.1, 23.1, 24.3, 24.31, 24.32, 24.33

(56) References Cited

U.S. PATENT DOCUMENTS

| | | |
|---|---|---|
| 4,908,319 A | 3/1990 | Smyczek et al. |
| 5,038,852 A | 8/1991 | Johnson et al. |
| 5,100,775 A | 3/1992 | Smyczek et al. |
| 5,143,854 A | 9/1992 | Pirrung et al. |
| 5,360,741 A | 11/1994 | Hunnell |
| 5,474,796 A | 12/1995 | Brennan |
| 5,492,806 A | 2/1996 | Drmanac et al. |
| 5,525,464 A | 6/1996 | Drmanac et al. |
| 5,541,061 A | 7/1996 | Fodor et al. |
| 5,545,531 A | 8/1996 | Rava et al. |
| 5,571,639 A | 11/1996 | Hubbell et al. |
| 5,578,832 A | 11/1996 | Trulson et al. |
| 5,580,717 A | 12/1996 | Dower et al. |
| 5,593,839 A | 1/1997 | Hubbell et al. |
| 5,599,695 A | 2/1997 | Pease et al. |
| 5,631,734 A | 5/1997 | Stern et al. |
| 5,681,529 A * | 10/1997 | Taguchi et al. ............... 422/61 |
| 5,695,940 A | 12/1997 | Drmanac et al. |
| 5,733,729 A | 3/1998 | Lipshutz et al. |
| 5,744,305 A | 4/1998 | Fodor et al. |
| 5,770,456 A | 6/1998 | Holmes |
| 5,834,758 A | 11/1998 | Trulson et al. |
| 5,837,832 A | 11/1998 | Chee et al. |
| 5,843,655 A | 12/1998 | McGall |
| 5,847,105 A | 12/1998 | Baldeschwieler et al. |
| 5,856,101 A | 1/1999 | Hubbell et al. |
| 5,856,174 A | 1/1999 | Lipshutz et al. |
| 5,861,242 A | 1/1999 | Chee et al. |
| 5,874,219 A | 2/1999 | Rava et al. |
| 5,882,930 A | 3/1999 | Baier |
| 5,922,591 A | 7/1999 | Anderson et al. |
| 5,945,334 A | 8/1999 | Besemer et al. |
| 5,948,673 A * | 9/1999 | Cottingham ............. 435/287.2 |
| 5,955,283 A | 9/1999 | Bandman et al. |
| 5,955,284 A | 9/1999 | Braxton et al. |

FOREIGN PATENT DOCUMENTS

| | | | |
|---|---|---|---|
| WO | WO 91/07087 | | 5/1991 |
| WO | WO97/02357 | * | 1/1997 |
| WO | WO 97/10056 A2 | | 3/1997 |
| WO | WO 99/19717 A1 | | 4/1999 |
| WO | WO 99/42558 A1 | | 8/1999 |

OTHER PUBLICATIONS

Rehman et al., "Immobilization of acrylamide–modified oligonucleotides by co–polumerization," Nucleic Acids Research, 27(2): 649–655 (1999).

* cited by examiner

*Primary Examiner*—Jeffrey Siew
(74) *Attorney, Agent, or Firm*—Robin M. Silva; Dorsey & Whitney LLP (57) ABSTRACT

The present invention provides a method and an improved apparatus for removing gas bubbles from a reaction chamber comprising a flexible layer removably affixed to a substrate layer having a multiplicity of oligonucleotide binding sites disposed thereon, in which biological reactions are performed. The invention specifically relates to methods and apparatus for removing gas bubbles from a reaction chamber wherein target molecules contained in a sample fluid are reacted with probe molecules immobilized on a substrate having an array of oligonucleotide binding sites. The arrays are covered with a flexible, gas permeable layer that permits mixing of the sample fluid on the biochip and removal of gas bubbles from the fluid by use of a means for facilitating diffusion of gas bubbles across the flexible, gas permeable layer.

8 Claims, 6 Drawing Sheets

METHOD AND APPARATUS FOR PERFORMING BIOLOGICAL REACTIONS ON A SUBSTRATE SURFACE

RELATED APPLICATIONS

This application is a continuation-in-part of U.S. application Ser. No. 09/464,490, filed Dec. 15, 1999, which is incorporated herein by reference.

BACKGROUND OF THE INVENTION

1. Field of the Invention

The present invention relates to an apparatus for performing biological reactions on a substrate surface and a method for removing gas bubbles from the apparatus. Specifically, the invention relates to an apparatus having a flexible, gas permeable layer affixed to a substrate layer with an adhesive, wherein the flexible, gas permeable layer, the adhesive and the substrate layer enclose a reaction chamber, and a means for facilitating diffusion across the flexible, gas permeable layer. The diffusion-facilitating means creates a pressure gradient or concentration gradient across the flexible, gas permeable layer, thereby increasing the rate of diffusion of gas molecules from the reaction chamber across the flexible, gas permeable layer.

2. Description of the Prior Art

Recent advances in molecular biology have provided the opportunity to identify pathogens, diagnose disease states, and perform forensic determinations using gene sequences specific for the desired purpose. This explosion of genetic information has created a need for high-capacity assays and equipment for performing molecular biological assays. Most urgently, there is a need to miniaturize, automate, standardize and simplify such assays. While these assays were originally developed in research laboratories working with purified products and performed by highly skilled individuals, adapting these procedures to clinical uses, such as diagnostics, forensics and other applications, has produced the need for equipment and methods that allow less-skilled operators to effectively perform the assays under higher capacity, less stringent assay conditions.

Existing technology utilizes the binding of molecules contained within a biologically reactive sample fluid, hereinafter referred to as target molecules, onto molecules contained within biologically reactive sites, hereinafter referred to as probe molecules. The primary enabler of this technology is an apparatus commonly referred to as a biochip, which comprises one or more ordered microscopic arrays ("microarrays") of biologically reactive sites immobilized on the surface of a substrate. A biologically reactive site can be created by dispensing a small volume of a fluid containing a biological reagent onto a discrete location on the surface of a substrate, also commonly referred to as spotting. To enhance immobilization of probe molecules, biochips can include a 2-dimensional array of 3-dimensional polymeric anchoring structures (for example, polyacrylamide gel pads) attached to the surface of the substrate. Probe molecules such as oligonucleotides are covalently attached to polyacrylamide-anchoring structures by forming amide, ester or disulfide bonds between the biomolecule and a derivatized polymer comprising the cognate chemical group. Covalent attachment of probe molecules to such polymeric anchoring structures is usually performed after polymerization and chemical cross-linking of the polymer to the substrate is completed.

Biochips are advantageously used to perform biological reactions on the surface thereof. Existing apparatus for performing biological reactions on a substrate surface, however, are deficient in that they either require unacceptably large volumes of sample fluid to operate properly, cannot accommodate substrates as large as or larger than a conventional microscope slide, cannot independently accommodate a plurality of independent reactions, or cannot accommodate a substrate containing hydrogel-based microarrays. Most existing apparatus also do not allow introduction of fluids in addition to the sample fluid (such as wash buffers, fluorescent dyes, etc.) into the reaction chamber. Disposable apparatus must be disassembled and reassembled around the biochip every time a new fluid must be introduced. Other existing apparatus are difficult to use in a laboratory environment because they cannot be loaded with standard pipet tips and associated pipettor apparatus.

Many existing apparatus also exhibit unacceptable reaction reproducibility, efficiency, and duration. Reaction reproducibility may be adversely affected by bubble formation in the reaction chamber or by the use of biologically incompatible materials for the reaction chamber. Reaction duration and efficiency may be adversely affected by the presence of concentration gradients in the reaction chamber.

Bubbles can form upon introduction of sample fluid to the reaction chamber or by outgassing of the reaction chamber materials. When gas bubbles extend over the substrate surface in an area containing biologically reactive sites, the intended reaction may intermittently fail or yield erroneous results because the intended concentration of the sample fluid mixture has been compromised by the presence of gas bubbles.

Biologically incompatible reaction chamber materials may cause unacceptable reaction reproducibility, by interacting with the sample fluid, thus causing the intended reaction to intermittently fail or yield erroneous results.

Incomplete mixing of the sample fluid can introduce concentration gradients within the sample fluid that adversely impact reaction efficiency and duration. This effect is most pronounced when there is a depletion of target molecules in the local volume surrounding a biologically reactive site. During a biological reaction, the probability that a particular target molecule will bind to a complementary (immobilized) probe molecule is determined by the given concentration of target molecules present within the sample fluid volume, the diffusion rate of the target molecule through the reaction chamber, and the statistics of interaction between the target molecule and the complementary probe molecule. For diagnostic assays, target DNA molecules are often obtained in minute (<picomol) quantities. In practice, it can take tens of hours for a hybridization reaction to be substantially complete at the low target nucleic acid molecule levels available for biological samples. Concentration gradients in the hybridization chamber can further exacerbate this problem.

U.S. Pat. No. 5,948,673 to Cottingham discloses a self-contained multi-chamber reactor for performing both DNA amplification and DNA probe assays in a sealed unit wherein some reactants are provided by coating the walls of the chambers and other reactants are introduced into the chambers prior to starting the reaction in order to eliminate flow into and out of the chamber. No provisions are made for eliminating gas bubbles from the chambers.

There remains a need in the art for methods and apparatus for performing biological reactions on a substrate surface that use a low volume of sample fluid, that accommodate substrates as large as or larger than a conventional microscope slide, that accommodate a plurality of independent reactions, and that accommodate a substrate surface having one or more hydrogel-based microarrays attached thereto. There also remains a need in the art for an apparatus that allows introduction of fluids in addition to sample fluid into each reaction chamber via standard pipet tips and associated pipettor apparatus. There also remains a need in the art for such an apparatus that increases reaction reproducibility, increases reaction efficiency, and reduces reaction duration. There also remains a need in this art for a simple method for removing gas bubbles from such an apparatus. These needs are particularly striking in view of the tremendous interest in biochip technology, the investment and substantial financial rewards generated by research into biochip technology, and the variety of products generated by such research.

SUMMARY OF THE INVENTION

The invention provides an apparatus for performing biological reactions on a substrate surface and a method for removing gas bubbles from the apparatus to prevent interference with biological reactions such as hybridization at reaction sites on-the substrate surface. Specifically, the method of the invention is directed to an apparatus comprising a flexible, gas permeable layer affixed to a biochip with an adhesive, wherein the flexible, gas permeable layer, the adhesive, and the biochip enclose a reaction chamber, and a means for facilitating diffusion of gas molecules out of the reaction chamber across the flexible, gas permeable layer. The diffusion-facilitating means creates a pressure gradient or concentration gradient across the flexible, gas permeable layer, thereby increasing the rate of diffusion of gas molecules from the reaction chamber through the flexible, gas permeable layer.

The biochip comprises a substrate having a first surface and a second surface, wherein the first surface contains an array of biologically reactive sites, and is preferably an oligonucleotide array. The array is provided in an area bounded by an adhesive set down on the first substrate surface. The flexible, gas permeable layer, the adhesive and the first substrate surface further define a volume comprising a reaction chamber.

The flexible, gas permeable layer preferably is deformable, translucent, and porous. More preferably, the flexible, gas permeable layer is selectively permeable to gas but impermeable to liquid. Most preferably, the flexible, gas permeable layer is selectively permeable to gases and impermeable to liquids because the surface tension of the sample fluid prevents escape of the liquid through the pores of the flexible membrane.

In certain embodiments of the invention, the substrate comprises a multiplicity of oligonucleotide arrays, which are contained in one or a plurality of areas bounded by the adhesive and covered by the flexible, gas permeable layer.

Each of the reaction chambers also preferably include a first port, and certain embodiments further include a second port, that transverses the substrate and comprises a first opening on the first substrate surface and a second opening on the second substrate surface. The openings of these ports on the second substrate surface are covered by a removable cover, most preferably a foil tape. The openings of these ports on the first substrate surface are provided within the area bounded by the adhesive.

The adhesive, the flexible, gas permeable layer and the substrate also enclose a reaction chamber that is filled prior to use with a water-soluble compound. The water-soluble compound is preferably a solid at a temperature most preferably at or below room temperature, and a liquid at higher temperatures, most preferably below about 100° C.

In preferred embodiments, the diffusion-facilitating means creates a pressure differential across the flexible, gas permeable layer. In more preferred embodiments, the diffusion-facilitating means comprises a vacuum source removably affixed to the flexible, gas permeable layer, wherein the vacuum source is used to apply a vacuum to the flexible, gas permeable layer. Most preferably, the vacuum source comprises a vacuum pump connected by a length of plastic tubing to a reducer that completely encloses the area defined by the adhesive and is removably sealed to the flexible, gas permeable layer.

The chamber is also optionally supplied with a roller, most preferably a patterned roller, positioned in contact with the flexible, gas permeable layer and movable longitudinally across the surface of the chamber for mixing sample fluid and wash solutions as required.

Specific preferred embodiments of the present invention will become evident from the following more detailed description of certain preferred embodiments and the claims.

DESCRIPTION OF THE DRAWINGS

Presently preferred embodiments of the invention are described with reference to the following drawings.

FIGS. 1A–1D are views of an illustrative embodiment of the present invention illustrating the preparation of a chamber of the invention for reaction.

DESCRIPTION OF THE PREFERRED EMBODIMENTS

The present invention provides an apparatus for performing high-capacity biological reactions on a biochip comprising a substrate having an array of biological binding sites. The invention also provides a method for removing gas bubbles from the apparatus. The invention is specifically directed to methods for removing gas bubbles from an apparatus comprising a reaction chamber having one or more arrays, preferably comprising arrays consisting of gel pads, and most preferably comprising arrays consisting of 3-dimensional polyacrylamide gel pads, wherein biological reactions are performed by reacting a biological sample containing a target molecule of interest with a complementary probe molecule immobilized on the biochip.

As used herein, the term "array" refers to an ordered spatial arrangement, particularly an arrangement of immobilized biomolecules or polymeric anchoring structures.

As used herein, the term "addressable array" refers to an array wherein the individual elements have precisely defined x and y coordinates, so that a given element at a particular position in the array can be identified.

As used herein, the terms "probe" and "biomolecular probe" refer to a biomolecule used to detect a complementary biomolecule. Examples include antigens that detect antibodies, oligonucleotides that detect complimentary oligonucleotides, and ligands that detect receptors. Such probes are preferably immobilized on a substrate.

As used herein, the terms "bioarray," "biochip" and "biochip array" refer to an ordered spatial arrangement of immobilized biomolecules or polymeric anchoring structures on a solid supporting substrate. Preferred probe molecules include nucleic acids, oligonucleotides, peptides, ligands, antibodies and antigens; oligonucleotides are the most preferred probe species.

The invention is advantageously used for performing biological reactions using biochips 18, preferably at room temperature or at slightly elevated temperatures. Biochips, as used in the art, encompass substrates containing arrays or microarrays, preferably ordered arrays and most preferably ordered, addressable arrays, of biological molecules that comprise one member of a biological binding pair. Typically, such arrays are oligonucleotide arrays comprising a nucleotide sequence that is complementary to at least one sequence that may be or is expected to be present in a biological sample. Alternatively, peptides or other small molecules can be arrayed in such biochips for performing, inter alia, immunological analyses (wherein the arrayed molecules are antigens) or assaying biological receptors (wherein the arrayed molecules are ligands, agonists or antagonists of said receptors).

One characteristic of biochips is the manner in which the arrayed biomolecules are attached to the surface of the biochip. Conventionally such procedures involve multiple reaction steps, often requiring chemical modification of the solid support itself. Even in embodiments comprising absorption matrices, such as hydrogels, present on a solid support, chemical modification of the gel polymer is necessary to provide a chemical functionality capable forming a covalent bond with the biomolecule. The efficiency of the attachment chemistry and strength of the chemical bonds formed are critical to the fabrication and ultimate performance of the microarray.

Preferably, polyacrylamide hydrogels and gel pads are used as binding layers to adhere biological molecules to surfaces, wherein said biological molecules include but are not limited to small molecule ligands, hormomes, nutrients, metabolites, proteins, peptides, oligonucleotides, polynucleotides, and larger nucleic acid fragments. The gel pads for use with the apparatus of the present invention are conveniently produced as thin sheets or slabs, typically by depositing a solution in between two glass surfaces (such as glass plates or microscope slides) using a spacer to obtain the desired thickness of the polyacrylamide gel, wherein the solution comprises a monomer, most preferably an acrylamide monomer, a crosslinker such methylene bisacrylamide, a catalyst such as N,N,N',N'-tetramethylethylendiamine (TEMED) and an initiator such as ammonium persulfate for chemical polymerization, or 2,2-dimethoxy-2-phenyl-acetophone (DMPAP) for photopolymerization. Generally, the acrylamide monomer and crosslinker are prepared in a solution of about 4–5% acrylamide (having an acrylamide/bisacrylamide ratio of 19:1) in water/glycerol, with a small amount of initiator added. The solution is polymerized and crosslinked either by ultraviolet (UV) radiation (e.g., 254 nm for at least about 15 minutes, or other appropriate UV conditions, collectively termed "photopolymerization"), or by thermal initiation at elevated temperature (e.g., typically at about 40° C.). Following polymerization and crosslinking, the top glass slide is removed from the surface to uncover the gel. The pore size (and hence the "sieving properties") of the gel can be controlled by changing the amount of crosslinker and the percent of the monomer in the polymerization solution. The pore size also can be controlled by changing the polymerization temperature.

In the fabrication of polyacrylamide hydrogel arrays (i.e., patterned gels) used as binding layers for biological molecules, the acrylamide solution typically is imaged through a mask during the UV polymerization/crosslinking step. The top glass slide is removed after polymerization, and the unpolymerized monomer is washed away (developed) with water, leaving a fine feature pattern of polyacrylamide hydrogel, which is used to produce the crosslinked polyacrylamide hydrogel pads. Further, in an application of lithographic techniques known in the semiconductor industry, light can be applied to discrete locations on the surface of a polyacrylamide hydrogel to activate these specified regions for the attachment of an oligonucleotide, an antibody, an antigen, a hormone, hormone receptor, a ligand or a polysaccharide on the surface (e.g., a polyacrylamide hydrogel surface) of a solid support (see, for example, International Application, Publication No. WO 91/07087, incorporated by reference).

For hydrogel-based arrays using polyacrylamide, biomolecules (such as oligonucleotides) are covalently attached by forming an amide, ester or disulfide bond between the biomolecule and a derivatized polymer comprising the appropriate cognate chemical group. Covalent attachment of the biomolecule to the polymer is usually performed after polymerization and chemical cross-linking of the polymer is completed.

Alternatively, oligonucleotides bearing 5'-terminal acrylamide modifications can be used that efficiently copolymerize with acrylamide monomers to form DNA-containing polyacrylamide copolymers (Rehman et al., 1999, *Nucleic Acids Research* 27: 649–655). Using this approach, stable probe-containing layers can be fabricated on supports (e.g., microtiter plates and silanized glass) having exposed acrylic groups. This approach has been commercially marketed as "Acrydite™" capture probes (available from Mosaic Technologies, Boston, Mass.). The Acrydite moiety is a phosporamidite that contains an ethylene group capable of free-radical copolymerization with acrylamide, and which can be used in standard DNA synthesizers to introduce copolymerizable groups at the 5' terminus of any oligonucleotide probe.

With reference to the illustration provided in FIG. 1, the invention provides an apparatus 10 comprising a biochip, which itself comprises a substrate 11 having a first surface 12 and a second surface 13 opposite thereto, and a flexible, gas permeable layer 16 affixed to the first substrate surface 12 by an adhesive 15. On the first surface 12 is an area 14 bounded by adhesive 15 and completely covered by flexible, gas permeable layer 16. Flexible, gas permeable layer 16, adhesive 15, and first substrate surface 12 enclose a volume or reaction chamber 25. The ratio of volume 25 to area 14 is preferably from about 0.025 µL/mm² to about 0.25 µL/mm², more preferably from about 0.1 µL/mm² to about 0.25 µL/mm², and most preferably from about 0.1 µL/mm² to about 0.2 µL/mm².

Figure 2:
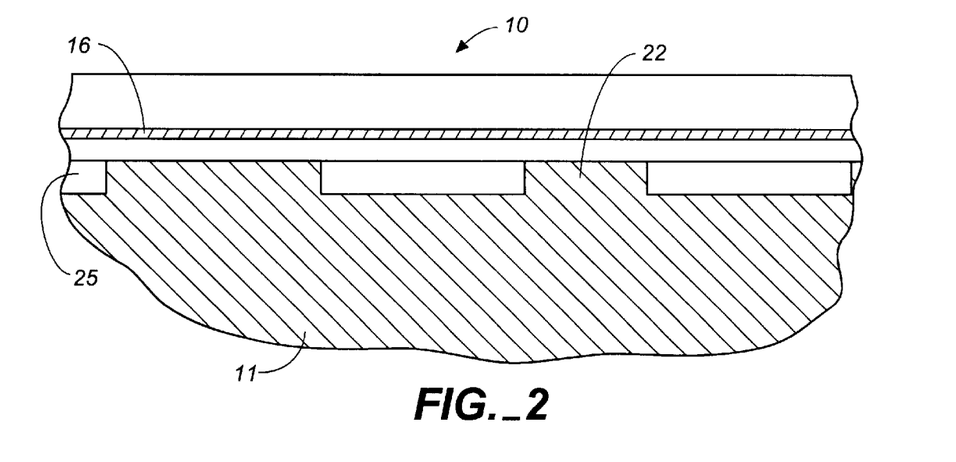
FIG. 2 is an exploded perspective view of the array of biomolecular probes showing the positioning of the gel pads on the substrate of a preferred embodiment of the invention.
Figure 3:
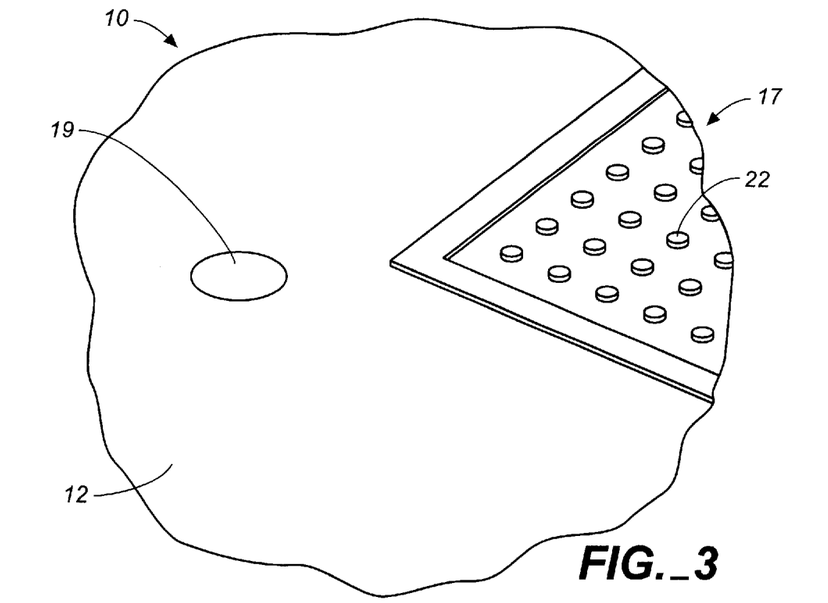
FIG. 3 is an exploded cross-sectional view of a chamber showing the array of gel pads of a preferred embodiment of the invention.

As shown in FIG. 2, an array 17 of biomolecules, which is preferably affixed to first substrate surface 12, is positioned between flexible, gas permeable layer 16 and first substrate surface 12 in area 14. In preferred embodiments, the array comprises at least about 400, more preferably at least about 1000, and most preferably at least about 10,000 biomolecular probes. Array 17 most preferably further comprises gel pads 22. FIG. 3 provides an exploded cross-sectional view of a portion of array 17 illustrating the gel pads 22. Each gel structure 22 is preferably cylindrical, most preferably having about a diameter of about 100 microns and a thickness of about 25 microns. The distance between each site within each array 17 is most preferably about 300 microns.

Figure 1A:
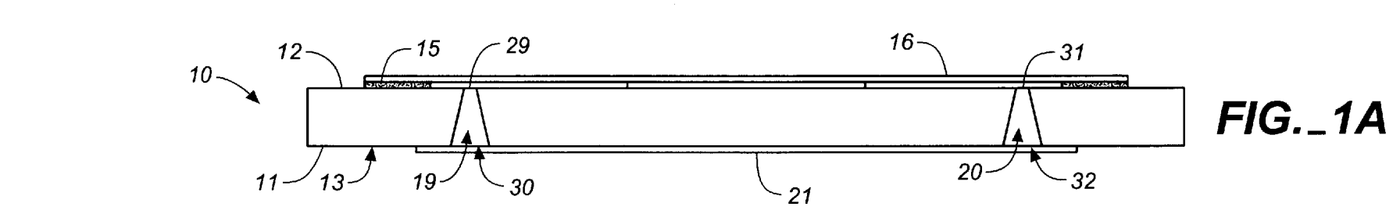
FIG. 1A is a cross-sectional view of the apparatus illustrating a reaction chamber prefilled with a water-soluble compound.

A layer of a water-soluble compound 28 having a melting point of about 30° C. to about 60° C., more preferably of about 35° C. to about 50° C., and most preferably of about 35° C. to about 45° C. is deposited in volume 25 bounded by first substrate surface 12, flexible, gas permeable layer 16, and adhesive 15. Preferably, the water-soluble compound is biocompatible, does not stick to or clog the pores of flexible, gas permeable layer 16, and serves to prevent mechanical damage to gel pads 22. In a preferred embodiment, the compound is polyethylene glycol, most preferably polyethylene glycol 600. The compound 28 is deposited so that the entire volume 25, with the exception of that portion of volume 25 occupied by array 17, comprises compound 28.

Array 17 can be positioned on surface 12 by providing markings, most preferably holes or pits in surface 12, that act as fiducials or reference points on surface 12 for accurate placement of array 17. The presence of said fiducials is particularly advantageous in embodiments comprising a multiplicity of arrays 17 in one or a multiplicity of areas 14 on surface 12, wherein accurate placement of said arrays is required for proper spacing and orientation of the arrays on the reaction chamber.

Figure 1B:
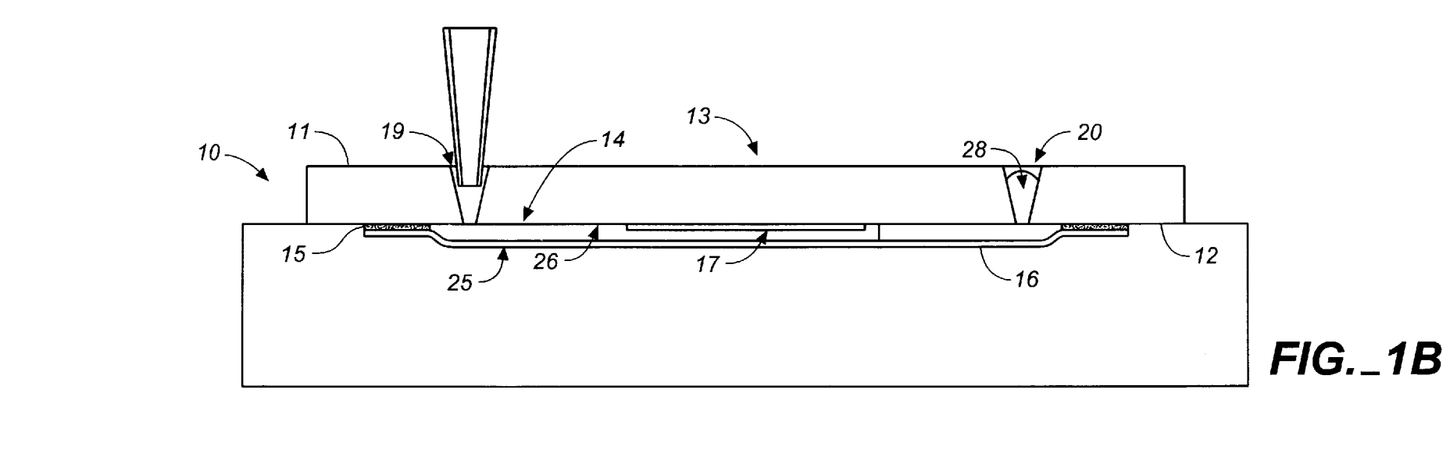
FIG. 1B is a cross-sectional view of the apparatus illustrating the mixing of the water-soluble compound and the biological sample fluid.
Figure 1C:
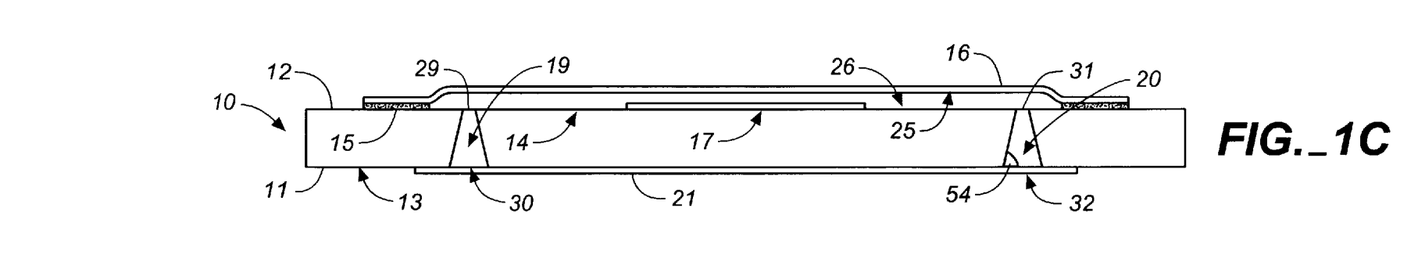
FIG. 1C is a cross-sectional view of the apparatus illustrating a chamber filled with the sample fluid/water-soluble compound mixture, wherein the first and second ports are covered with a seal.

Substrate 11 further comprises a first port 19 that transverses the substrate from the first surface 12 to the second surface 13 and forms first and second openings 29 and 30 on said first and second surfaces, respectively. The first port 19 serves as an input port and is positioned in substrate 11 so that the first opening 29 is provided within the area 14 bounded by adhesive 15 on first surface 12. In further preferred embodiments, substrate 11 further comprises a second port 20 that transverses the substrate from first surface 12 to second surface 13 and forms first and second openings 31 and 32 on said first and second surfaces, respectively. Second port 20 serves as an outlet port and is positioned in substrate 11 so that the first opening 31 opens within area 14 bounded by the adhesive 15 on the first surface 12. The second openings of ports 19 and 20 are covered with a removable and replaceable cover 21. In preferred embodiments, replaceable cover 21 is a stopper, a gasket, or tape, most preferably foil tape.

Figure 4:
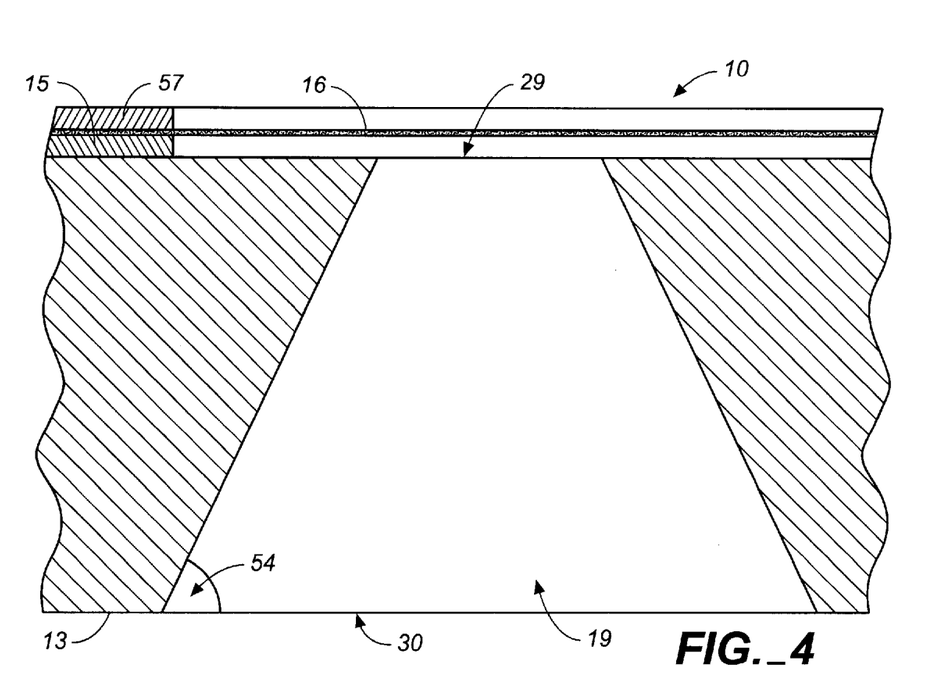
FIG. 4 is an exploded cross-sectional view of a port illustrating the conical shape of the port of a preferred embodiment of the invention.

Input and output ports 19 and 20 are preferably shaped to accept a plastic pipette tip, most preferably a 10 µL pipette tip or a 200 µL pipette tip. In preferred embodiments, input and output ports 19 and 20 are generally in the shape of a truncated cone, as shown in FIG. 4, wherein the end of the cone having the smaller diameter forms the first opening of each port 29 and 31, respectively, and the end of the cone having the larger diameter forms the second opening of each port 30 and 32, respectively. This shape creates a seal between the pipette tip and the port, enhances visibility of the port for operator accuracy and prevents protrusion of the pipette tip into volume 25, thereby preventing potential damage to components therein, particularly the flexible, gas permeable layer 16. In these embodiments, each port preferably has a diameter on second substrate surface 13 of from about 1.0 mm to about 2.0 mm, and a diameter on first substrate surface 12 of from about 0.3 mm to about 0.6 mm. The conical walls of ports 19 and 20 form an angle 54 with the second substrate surface 13, which is preferably less than 90°. Most preferably, angle 54 is less than or equal to the contact angle 55 of the biological sample fluid 26. Most preferably, angle 54 is equal to contact angle 55 such that the surface of the fluid in the port is flat. For aqueous solutions, this angle is about 60°. This geometric arrangement provides a port that tends not to leak, but instead wicks fluid into volume 25 so that the second substrate surface 13 is dry when replaceable cover 21 is applied.

Substrate 11 is fabricated from any solid supporting substance, including but not limited to plastics, metals, ceramics, and glasses. Most preferably, substrate 11 is made from silicon or glass (for accuracy and stiffness), molded plastics (which reduce cost of manufacture and thermal inertia), or ceramics (for the incorporation of microfluidic elements including integrated heating elements). Most preferably, substrate 11 is glass.

Figure 1D:
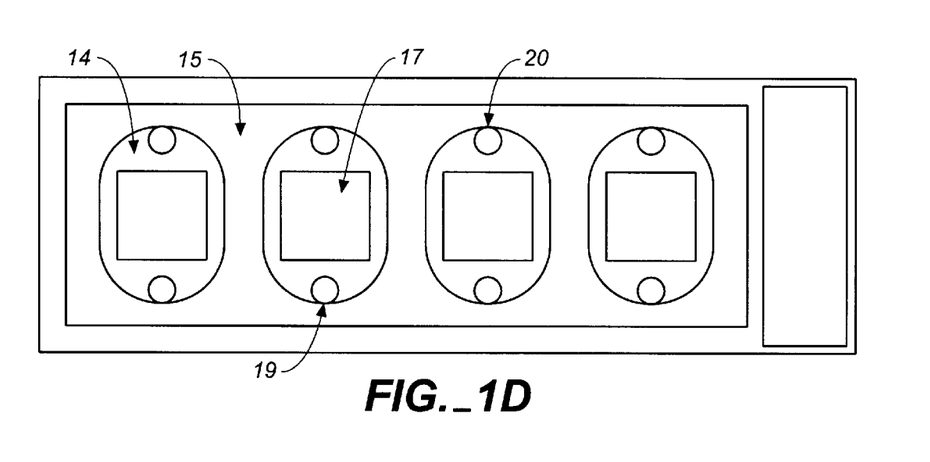
FIG. 1D is a top plan view of the apparatus illustrating the pattern of adhesive defining the individual areas containing the arrays of oligonucleotide probes.

Adhesive 15 is prepared using an adhesive suitable for forming a water-tight bond between substrate 11 and flexible, gas permeable layer 16, including, but not limited to, high temperature acrylics, rubber-based adhesives, and silicone-based adhesives. The shape of adhesive 15 is configured to contain array 17. Adhesive 15 can be deposited on first substrate surface 12 in a pattern to produce area 14 in any desired shape, and is most preferably deposited to define an ellipsoidal area 14. Adhesive 15 can be deposited using inkjet printing or offset printing methods, or by die cutting the desired shapes from a sheet of adhesive material. In addition, a substantial portion of first surface 12 can be covered with adhesive and portions of the substrate which are not desired to retain adhesive properties can be hardened preferentially, for example, by ultraviolet curing. In these embodiments, portions retaining adhesive properties can be defined using a mask and thereby retain adhesive properties necessary to affix flexible, gas permeable layer 16 to surface 12. In embodiments using the die cut adhesive material, the adhesive material is preferably a double sided adhesive tape, and more preferably a double sided adhesive tape having no carrier. Adhesive 15 is most preferably set down in a layer between 1 and 100 µm thick, more preferably between 25 and 75 µm thick, and most preferably about 50 µm thick.

Flexible, gas permeable layer 16 preferably covers an area of from about 5 mm² to about 1400 mm², more preferably from about 5 mm² to about 600 mm², and most preferably from about 100 mm² to about 600 mm². Flexible, gas permeable layer 16 is made of any flexible solid substance, including but not limited to plastics, including polypropylene, polyethylene, and polyvinylidene chloride (sold commercially as Saran® wrap) plastics, rubbers, including silicone rubbers, high temperature polyesters, and porous TEFLON® (polytetrafluoroethylene). Flexible, gas permeable layer 16 is preferably deformable, porous, and biocompatible. Flexible, gas permeable layer 16 also preferably impermeable to liquids in order to prevent evaporation of water from the volume contained between the flexible, gas permeable layer and the substrate. Most preferably, flexible, gas permeable layer 16 is selected to have physical, chemical and mechanical properties such that the surface tension of sample fluid 26 prevents passage of the sample fluid through the pores of the membrane, while allowing passage of gas molecules across the flexible, gas permeable layer. Preferably, the pore size of flexible, gas permeable layer 16 is between 0.2 and 3.0 µm, more preferably between 0.2 and 1 µm, and most preferably about 0.2 µm. Flexible, gas permeable layer 16 also preferably is translucent and should be able to withstand temperatures of between 50° C. and 95° C. for a period of between 8 and 12 hours without shrinkage. In a preferred embodiment, the flexible, gas permeable layer is porous TEFLON®. Membranes having these characteristics are available from Pall Specialty Materials.

Figure 5:
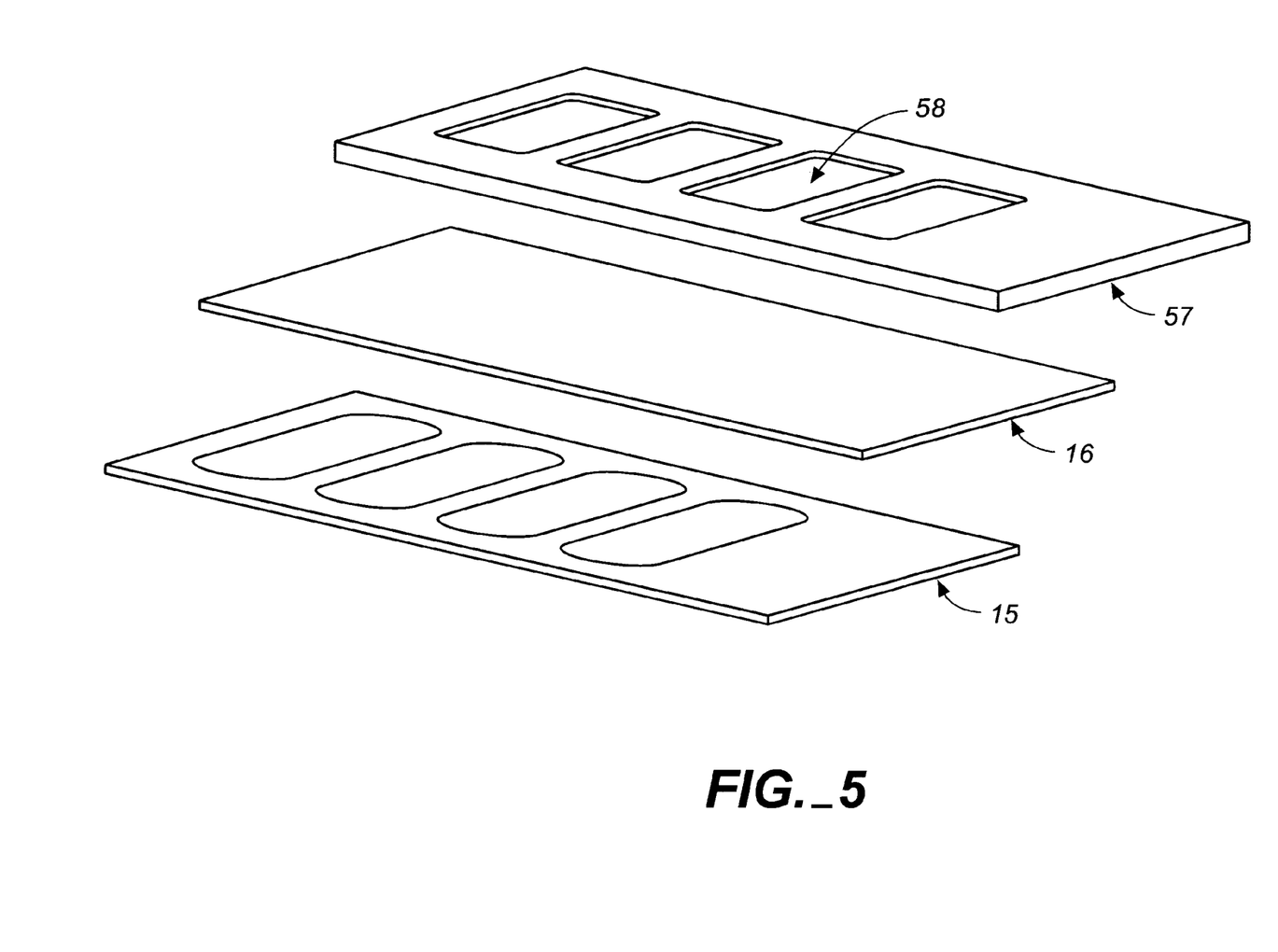
FIG. 5 is a perspective view of the label layer, the flexible, gas permeable layer and the adhesive of a preferred embodiment of the invention.

In preferred embodiments, as shown in FIG. 5, the invention further comprises a label layer 57 which is die cut in the same manner as the adhesive to form windows 58 that correspond in location to areas 14 on first substrate surface 12. The label layer is preferably a thick film having a layer of adhesive, and most preferably is an Avery laser label. The label layer is applied to the outer surface of the flexible, gas permeable layer, preferably by vacuum lamination. Areas 14 are visible through windows 58 in label layer 57.

Figure 6:
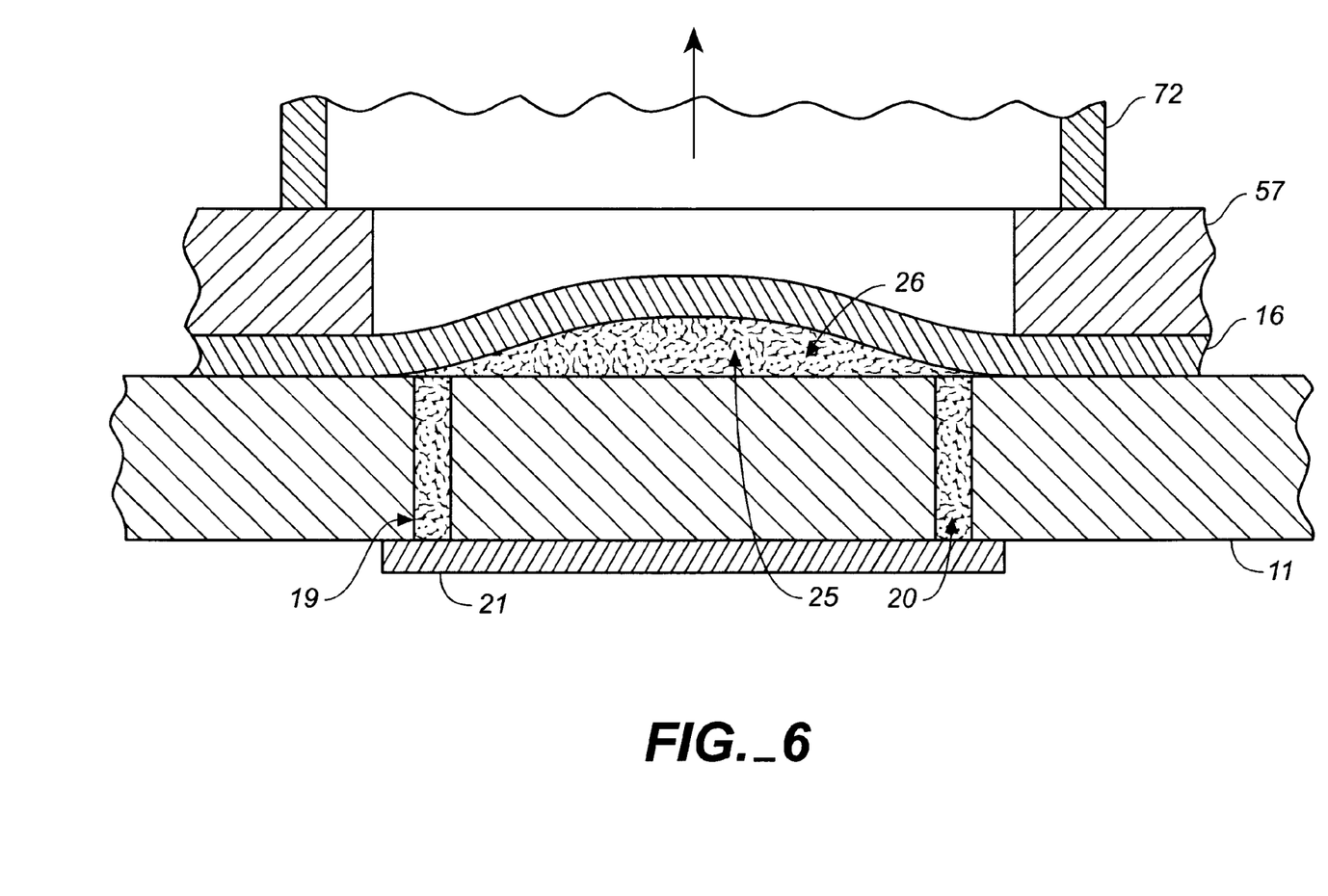
FIG. 6 is a cross-sectional view of a preferred embodiment of the present invention illustrating the application of vacuum to a reaction chamber.

A means for facilitating diffusion across the flexible, gas permeable layer is removably affixed to the flexible, gas permeable layer, or the label layer when present, in order to remove gas bubbles from the reaction chambers. The diffusion-facilitating means creates a pressure gradient or concentration gradient across flexible, gas permeable layer 16, thereby increasing the rate of diffusion of gas molecules from the sample fluid 26 contained in volume 25 across flexible, gas permeable layer 26. A preferred embodiment of the diffusion-facilitating means, wherein the diffusion-facilitating means creates a pressure gradient across flexible, gas permeable layer 16, is shown in FIG. 6. In this embodiment, a vacuum source 70 is removably affixed to flexible, gas permeable layer 16. In preferred embodiments, vacuum source 70 comprises a vacuum pump 71, a chamber seal 72 that completely surrounds area 14 and is removably affixed to flexible, gas permeable layer 16, and a length of plastic tubing 73 connecting vacuum pump 71 to reducer 72. The chamber seal may be a suction cup, a reducer, or any other structure having similar chemical and mechanical properties. Most preferably, the plastic tubing is polyurethane tubing. Most preferably the chamber seal is made of polyvinylidene fluoride (sold under the name Kynar® by Elf Atochem North America).

Diffusion-facilitating means that create a concentration gradient across the membrane are also preferred. Concentration gradients are created, for example, by providing a flow of inert gas across flexible, gas permeable layer 16, wherein the molecules of the inert gas are too large to pass through flexible, gas permeable layer 16, while the gas contained in volume 25 passes freely through flexible, gas permeable layer 16. Those skilled in the art will be able to select the characteristics of flexible, gas permeable layer 16 and diffusion-facilitating means that are appropriate for their selected sample fluid 26.

Array 17 contained in area 14 on first substrate surface 12 is covered with a water-soluble compound 28, which protects and seals the biochip prior to use and prevents degradation or other damage to the array. Any water-soluble compound 28 having a melting point of about 30° C. to about 60° C., more preferably of about 35° C. to about 50° C., and most preferably of about 35° C. to about 45° C. is advantageously used in filling volume 25 between array 17 and flexible, gas permeable layer 16. Preferably, the compound is polyethylene glycol, most preferably polyethylene glycol 600. It is a particularly preferred feature of reaction apparatus 10 of the invention that water-soluble compound 28 fills the entirety of the volume 25 and more preferably also fills at least a portion of input port 19. This inhibits formation of air bubbles in volume 25 because compound 28 is first melted, then carefully mixed with sample fluid 26 within volume 25 using a roller 40 without producing air bubbles in sample fluid 26. The lack of air bubbles in volume 25 enhances efficiency of the biological reaction by ensuring that interactions, such as hybridization, between the target molecules in the sample and probe molecules comprising the array 17 or gel pads of biochip 18 are capable of proceeding without interference from such air bubbles.

Alternative embodiments of the reaction apparatus 10 of the invention encompass a multiplicity of arrays 17 confined in a multiplicity of areas 14 underneath flexible, gas permeable layer 16, each area comprising an array 17 and being supplied with first port 19 and, optionally, second port 20. In these embodiments, adhesive 15 is deposited on first substrate surface 12 in a pattern that defines each of areas 14, and flexible, gas permeable layer 16 is applied to adhesive 15 to encompass areas 14 on said surface.

In certain embodiments of the invention, reaction apparatus 10 is produced containing array 17 or a multiplicity of arrays 17 as disclosed herein, wherein the chamber is provided ready-to-use by the addition of sample fluid 26 comprising one or a multiplicity of target molecules. In alternative embodiments, reaction apparatus 10 is provided without array 17, and permits insertion thereof by a user. In these embodiments, at least one edge of flexible, gas permeable layer 16 is not adhered to first substrate surface 12 until array 17 is inserted.

In the use of the reaction apparatus 10 of the invention, an amount of a sample fluid 26, most preferably comprising a biological sample containing a target molecule, is added to the reaction chamber through first port 19. Before application of the sample fluid 26 to the chamber, volume 25 is most preferably heated to a temperature greater than or equal to the melting temperature of water-soluble compound 28. When melted, sample fluid 26 can be added to the chamber and mixed with the water-soluble compound, as shown in FIG. 1B. Preferably, water-soluble compound 28 does not adversely affect the reaction taking place in the chamber. More preferably, the amount of compound 28 is chosen such that the efficiency of the biological reaction is improved when compound 28 is mixed with sample fluid 26.

In embodiments of the chamber comprising first port 19 but not second port 20, the sample fluid is preferably introduced into the chamber after compound 28 is melted, and then the fluid is cycled into and out of the chamber, most preferably using a pipette, until fluid 26 and compound 28 are fully mixed, and the sample fluid evenly distributed over the surface of array 17, or mixed into gel pads 22 comprising certain embodiments of said arrays. Alternatively, sample fluid 26 is evenly distributed over the surface of array 17, or mixed into gel pads 22 by physically manipulating flexible, gas permeable layer 16, as more fully described below. In these embodiments, sample fluid 26 is removed after the reaction is completed, and array 17 is washed by the cycling a sufficient volume of a wash solution 27 into and out of the chamber, most preferably using a pipette.

In embodiments of the chamber comprising both first port 19 and second port 20, the sample fluid is preferably introduced into the chamber after compound 28 is melted, and then the fluid is cycled into and out of the chamber, most preferably using at least one pipette, until fluid 26 and compound 28 are fully mixed, and the sample fluid evenly distributed over the surface of array 17, or mixed into gel pads 22 comprising certain embodiments of said biochips. Sample fluid 26 is removed after the reaction has been completed using outlet port 20, and the biochip washed by the addition and cycling of a sufficient volume of a wash solution 27 into and out of the chamber, most preferably using a pipette. In these embodiments, the wash solution can also be continuously provided by addition through the input port and removal through the output port. In certain embodiments, biochip 18 containing array 17 is removed from the chamber for development or further manipulations as required.

Prior to commencing the reaction, the reaction apparatus 10 is degassed using vacuum source 70. Preferably a vacuum of between 13 and 27 kPa (100 to 200 torr), more preferably a vacuum of between 13 and 20 kPa (100 to 150 torr), and most preferably a vacuum of about 13 kPa (100 torr) is applied. Preferably the vacuum is applied for between 10 seconds and 2 minutes, more preferably between 10 seconds and 1 minute, most preferably between 10 seconds and 30 seconds. Vacuum source 70 is then detached from flexible, gas permeable layer 16, and volume 25 is visually inspected for the presence of gas bubbles.

The Examples that follow are illustrative of specific embodiments of the invention and various uses thereof. They are set forth for explanatory purposes only, and are not to be taken as limiting the invention.

EXAMPLE 1

Removing Gas Bubbles From of a Reaction Chamber

Figure 7:
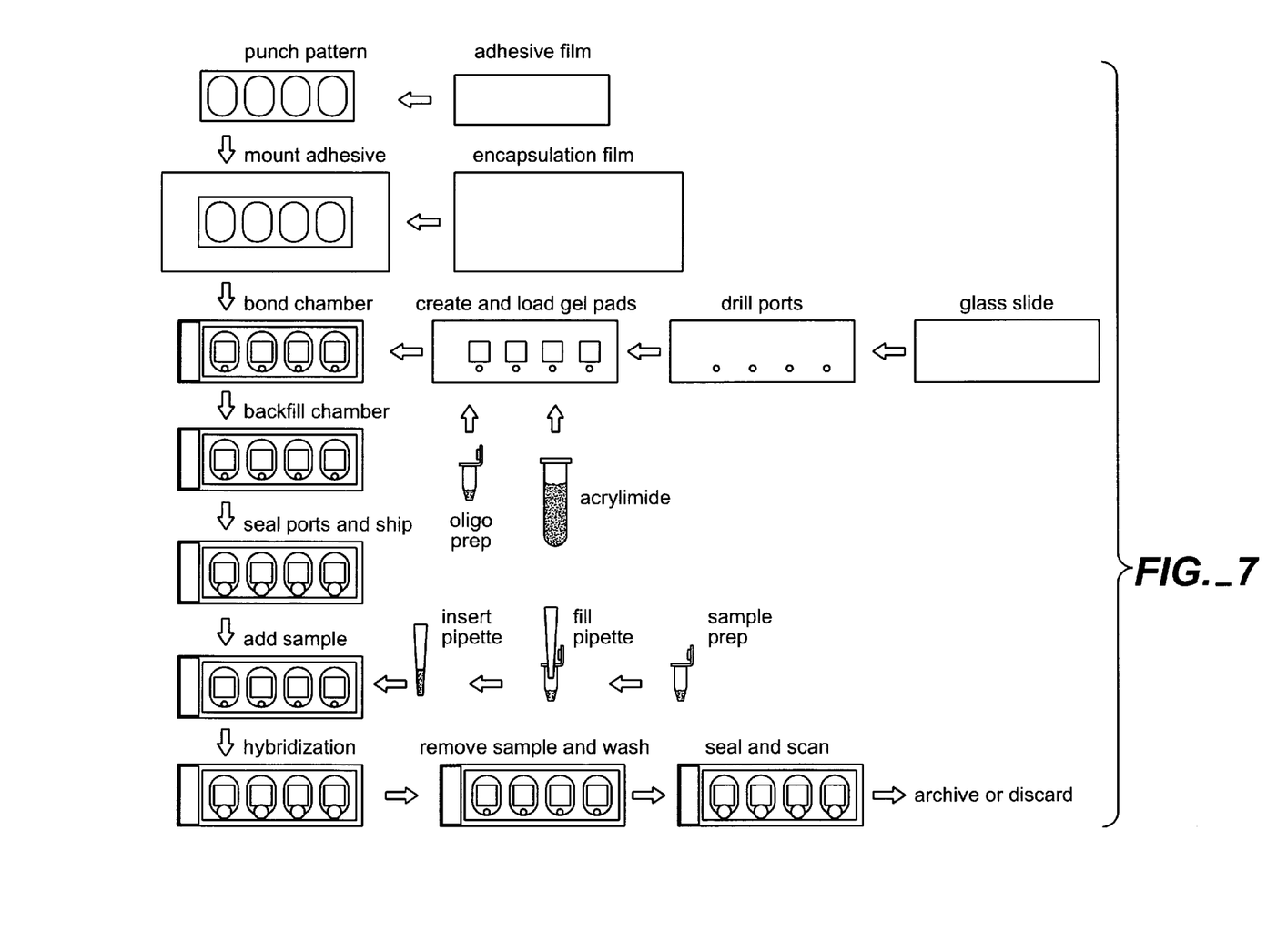
FIG. 7 illustrates the assembly and use of a preferred embodiment of the present invention.

The process of assembling a chamber according to the present invention is illustrated in FIG. 7.

A four reaction-chamber apparatus is manufactured using a layer of 0.2 μm porous Teflon unsupported membrane as the flexible, gas permeable layer, following the procedure provided in U.S. application Ser. No. 09/464,490, incorporated by reference herein. Each reaction chamber is filled with 75 μL of a sample fluid containing biological target molecules by injection through a 300 μL pipette tip (VWR Part No. 53510-084) using a 200 μL pipettor (Rainin P-200). Bubbles are visually detectable in the chambers after injection.

A reaction chamber is isolated by applying a Cole-Parmer Kynar ¼"×⅝" barbed reducer (Part No. 31513-31) directly to the frame layer and forming a seal around the chamber. A "house" vacuum source is connected to the reducer by a length of polyurethane tubing. A vacuum of 200 torr is applied for two minutes. Visual inspection of the chamber following application of the vacuum shows no gas bubbles remaining in the chamber.

The reaction apparatus is maintained at 25° C. and atmospheric pressure for 8 hours until the reaction proceeds to completion. No appreciable evaporation of water from the chamber is observed.

It should be understood that the foregoing disclosure emphasizes certain specific embodiments of the invention and that all modifications or alternatives equivalent thereto are within the spirit and scope of the invention as set forth in the appended claims.

What we claim is:

1. An apparatus for performing biological reactions, comprising:
    (a) a substrate having a first surface and a second surface opposite thereto,
    (b) an array of biomolecules positioned on the first surface of the substrate,
    (c) a flexible, gas permeable layer affixed to the first surface of the substrate by an adhesive, wherein the adhesive is deposited on the first surface of the substrate and encloses an area thereupon, and wherein the flexible, gas permeable layer, the adhesive, and the first substrate surface enclose a reaction chamber;
    (d) a port extending through the substrate from the first surface to the second surface thereof and having a first opening and a second opening, wherein the first opening of the port is provided within the area bounded by the adhesive and covered by the flexible, gas permeable layer and the second opening of the port is provided on the second surface of the substrate;
    (e) a removable cover positioned over the second opening of the port;
    (f) a layer of a water-soluble compound that is a solid at a first temperature and a liquid at a second, higher temperature, the layer being positioned in the reaction chamber between the first surface of the substrate and the flexible, gas permeable layer; and
    (g) a means for facilitating diffusion of gas bubbles across the flexible, gas permeable layer, wherein the diffusion-facilitating means creates a pressure gradient or concentration gradient across the flexible, gas permeable layer thereby increasing the rate of diffusion of gas bubbles from the reaction chamber across the flexible, gas permeable layer.

2. The apparatus of claim 1, wherein the flexible, gas permeable layer is a porous membrane.

3. The apparatus of claim 2, wherein the porous membrane is porous polytetrafluoroethylene.

4. The apparatus of claim 2, wherein, when the reaction chamber contains a fluid sample, the porous membrane prevents the sample fluid from passing through the membrane.

5. The apparatus of claim 1, wherein the means for facilitating diffusion of gas bubbles across the flexible, gas permeable layer comprises a vacuum source removably affixed to the flexible, gas permeable layer, and wherein the vacuum source is used to create a pressure gradient across the flexible, gas permeable layer to facilitate diffusion of gas bubbles from the reaction chamber across the flexible, gas permeable layer.

6. The apparatus of claim 5, wherein the vacuum source comprises:
    (a) a vacuum pump, and
    (b) a chamber seal removably affixed to the flexible, gas permeable layer and removably connected to the vaccum pump, wherein the seal completely surrounds the area on the first substrate surface containing the array of biomolecules.

7. In an apparatus for performing biological reactions, comprising a substrate having a first surface and a second surface opposite thereto, an array of biomolecules positioned on the first surface of the substrate, a flexible layer affixed to the first surface of the substrate by an adhesive, wherein the adhesive is deposited on the first surface of the substrate and encloses an area thereupon; a reaction chamber enclosed by the flexible layer, the adhesive and the first substrate surface; a port extending through the substrate from the first surface to the second surface thereof and having a first opening and a second opening, wherein the first opening of the port is provided within the area bounded by the adhesive and covered by the flexible layer and the second opening of the port is provided on the second surface of the substrate; a removable cover positioned over the second opening of the port; and a layer of a water-soluble compound that is a solid at a first temperature and a liquid at a second, higher temperature, the layer being positioned between the first surface of the substrate and the flexible layer, the improvement comprising (a) a flexible layer that is a gas permeable layer and
(b) a means for facilitating diffusion of gas bubbles across the flexible, gas permeable layer, wherein the diffusion-facilitating means creates a pressure gradient or concentration gradient across the flexible, gas permeable layer such that gas bubbles diffuse from the reaction chamber to the environment outside the flexible, gas permeable layer.

8. The improvement of claim 7, wherein the diffusion-facilitating means comprises a vacuum source removably affixed to the flexible, gas permeable layer and wherein the vacuum source is used to apply a vacuum to the flexible, gas permeable layer to remove gas bubbles from the reaction chamber.

* * * * *